United States Patent [19]

Toya et al.

[11] Patent Number: 5,002,775

[45] Date of Patent: Mar. 26, 1991

[54] TABLETS HAVING CLEAR IMPRESSED MARKS AND METHOD FOR MAKING SAME

[75] Inventors: Kazutoshi Toya, Takatsuki; Nobuo Uchiyama, Toyonaka; Seiko Miura, Takatsuki; Takayoshi Mitsunaga, Ibaraki; Hisao Tobiki, Kobe, all of Japan

[73] Assignee: Sumitomo Chemical Company, Limited, Osaka, Japan

[21] Appl. No.: 472,251

[22] Filed: Mar. 4, 1983

[30] Foreign Application Priority Data

Mar. 8, 1982 [JP] Japan ................................. 57-37046

[51] Int. Cl.$^5$ ................................. A61K 9/44
[52] U.S. Cl. ................................. 424/467; 424/7.1
[58] Field of Search ................. 424/6, 7.1; 427/3; 101/432, 170

[56] References Cited

U.S. PATENT DOCUMENTS

| | | | |
|---|---|---|---|
| 2,161,990 | 7/1939 | Asnes | 41/24 |
| 2,539,303 | 1/1951 | Gerke et al. | 101/4 |
| 2,687,367 | 8/1954 | Burrin | 424/7.1 |
| 2,865,810 | 12/1958 | Sanders | 424/6 |
| 2,925,365 | 2/1960 | Nicholson et al. | 167/82 |
| 2,996,431 | 8/1961 | Barry | 424/7.1 |
| 3,015,609 | 1/1962 | Sanders | 424/6 |
| 3,015,610 | 1/1962 | Sanders | 424/6 |
| 3,054,724 | 9/1962 | Raff | 167/82 |
| 3,125,490 | 3/1964 | Hershberg | 167/82 |
| 3,159,544 | 12/1964 | Heffernan et al. | 424/6 |
| 3,438,797 | 4/1969 | Biddle | 424/6 |
| 3,443,515 | 5/1969 | Smith et al. | 101/170 |
| 3,533,804 | 10/1970 | Bennett | 424/6 |
| 3,631,798 | 1/1972 | St. John | 101/170 |
| 3,633,502 | 1/1972 | Schwandt | 101/170 |
| 3,759,176 | 9/1973 | Schwandt | 101/170 |
| 3,981,984 | 9/1976 | Signorino | 424/33 |
| 4,066,585 | 1/1978 | Schepp et al. | 427/288 |
| 4,112,189 | 9/1978 | Terwilliger | 101/32 |
| 4,139,613 | 2/1979 | Hefele | 101/170 |
| 4,168,321 | 9/1979 | Okamoto . | |
| 4,212,899 | 7/1980 | Hodakowski et al. | 427/44 |
| 4,353,887 | 8/1980 | Hess et al. | 424/15 |
| 4,522,840 | 7/1985 | Corfield et al. | 427/3 |
| 4,661,367 | 5/1986 | Forse et al. | 427/3 |
| 4,720,378 | 1/1988 | Forse et al. | 424/6 |

FOREIGN PATENT DOCUMENTS

| | | |
|---|---|---|
| 0060023 | 9/1982 | European Pat. Off. . |
| 0088556 | 9/1983 | European Pat. Off. . |
| 0096982 | 12/1983 | European Pat. Off. . |
| 2820981 | 4/1979 | Fed. Rep. of Germany . |
| 3043914 | 6/1981 | Fed. Rep. of Germany . |
| 57-165314 | 12/1982 | Japan . |
| 58-152813 | 10/1983 | Japan . |
| 520 | of 1874 | United Kingdom ............ 424/6 |
| 2065691 | 7/1981 | United Kingdom . |

OTHER PUBLICATIONS

Moran, Printing in the 20th Century (1974), Hastings House, New York, N.Y., pp. 100–103, 272–284, 320–322 (Intaglio, Electrostatic, Driography).
Gross Etching Engraving & Intaglio Printing (1973), Oxford U. Press, N.Y., pp. 119–143 (Intaglio Printing, Intaglio Printing in color).
Abstract of U.S. Pat. No. 4,720,378, Official Gazzette, p. 1351 (Jan. 19, 1988).
Colorgon Opalux Oqaque Color Concentrate (1–81), 8 pp.
Porter D & Cl, May 1981, pp. 46, 48, 50, 53, 86–93, "Tablet Coating".
Porter D & Cl, Sep. 1981, pp. 50–54, 56, 58, "Tablet Coating".
Corfield et al., CA., 100, #126889y (1984), of EPO 96982, 12/28/83.
Kornblum et al., CA., 73, #59274g (1970), of J. Pharm. Sci., 59(7):1016–18 (1970).
Woznicki et al., CA., 91, #27306v (1979), of Ger. Off. 2820981, Apr. 5, 1979.
Signorino, CA., 85, #166660v (1976), of U.S. Pat. No. 3,981,854, Sep. 21, 1976.
Porter et al., CA., 95, #86324e (1981), of Ger. Off. 3,043,914, Jun. 19, 1981.
Porter, CA., 92, #220636b (1980), of Pharm. Technol., 4(3):67–75 (1980).
Rowe (1981), J. Pharm. Pharmacol., 33:1–4, The Effect of the Particle Size of an Inert Additive on the Surface Roughness of a Film-Coated Tablet.
Rowe et al. (1980), J. Pharm. Pharmacol., 32:647–648 (1980), The Effect of Film Thickness on the Incidence of the Defect Bridging of Intagliations on Film Coated Tablets.
Entwistle et al. (1979), J. Pharm. Pharmacol., 31:269–272, Plasticization of Cellulose Ethers Used in the Film Coatings of Tablets.
Rowe (1978), J. Pharm. Pharmacol., 30:343–346 (1978), The Measurement of the Adhesion of Film Coatings to Tablet Surfaces: Effect of Tablet Porosity Surface Roughness, Film Thickness.
Lehmann et al., Drugs Made in Germany (1973), 16:126, 131, 132, 134, 136, The Use of Aqueous Synthetic Polymer Dispersion for Coating Pharmaceutical Dosage Forms.
Porter, Pharm. Tech., 3(9):55–59 (1980), Aqueous Film Coating . . . An Overview.
Rowe et al., J. Pharm. Pharmacol., 33:174–175 (1981), The Effect of Plasticizer Type and Concentration on the Incidence of Bridgings of Intagliations On-Film-Coated Tablets.
Oxford English Dictionary (vol. V, H–K), p. 365; Intagliated, Intagliature, Intaglio.

*Primary Examiner*—Shep A. Rose
*Attorney, Agent, or Firm*—Cushman, Darby & Cushman

[57] ABSTRACT

Disclosed are tablets having clear marks including letters, figures and the like which are impressed thereon wherein a material different in color tone from the portion other than the mark portion is deposited in the impressed valley portion and if necessary, these tablets are further applied with a coating and a method for producing the tablets.

10 Claims, No Drawings

TABLETS HAVING CLEAR IMPRESSED MARKS AND METHOD FOR MAKING SAME

This invention relates to tablets having clear marks (including letters, figures and the like) impressed thereon and a method for producing same. More particularly, it relates to tablets having marks impressed thereon wherein in the impressed valley portion is deposited a material different in color tone from the portion other than the mark portion and, if necessary, these tablets are further applied with a coating and a method for producing same.

Generally, tablets are impressed with marks and the like for identification of kinds and contents of ingredients and names of makers, etc. and in some case the identification is made by observing the marks appearing on the surface of a film coated on tablets which have been impressed with the marks.

Such identification has the defects that it is difficult because letters or marks are shown only by the irregularity of the surface of tablets which is produced by impressing the letters or the marks and besides, when a coating film is provided thereon, the coating cannot be made in a large amount because the impressed valley portions are filled with the coating agent.

Another method of identification is to print the letters or marks on the surface of tablets which have been applied with a coating. This method also has the problems that the printing ink often falls off due to friction between tablets per se during the handling to result in unclear printed letters and marks and furthermore to cause stains on other tablets and that the tablets per se may stick to off-set roll due to low peeling property between the coating on the surface of the tablets and the printing ink.

The object of this invention is to provide tablets with clear impressed marks, letters, etc. which have no problems mentioned above and a method for producing them.

The above object has been attained by depositing in the impressed valley portion a material different in color tone from the portion other than the mark portion of the tablets and, if necessary, thereafter providing a coating on the tablets.

This invention will be explained in detail.

The material to be used in this invention which is deposited in the impressed valley portion and which has different color tone from the portion other than valley portion has no limitation as long as it is the one usually used as coatings or is an additive usually used for tablets and the like. This material will be called merely "deposition material" hereinafter. This deposition material can be used alone or as a mixture of two or more. Usually, the additive to which a coloring matter is added to differentiate the color of the valley portion from that of other portion is used as the deposition material. In short, it is necessary that the color tone of the material is different from that of the portion other than the mark portion. As examples of the material, mention may be made of powdery substances or powders, e.g., starches such as corn starch, wheat starch, potato starch, etc., sugars such as lactose, sucrose, mannitol, etc., inorganic coloring matters such as calcium sulfate, calcium phosphate, calcium carbonate, magnesium carbonate, magnesium silicate, magnesium oxide, aluminum hydroxide, titanium oxide, talc, kaolin, bentonite, etc., celluloses such as methyl cellulose, ethyl cellulose, carboxymethylethyl cellulose, hydroxypropylmethyl cellulose, hydroxypropylmethyl cellulose phthalate, hydroxypropyl cellulose, crystalline cellulose, etc., coloring agents such as food dyes, food lake dyestuff, etc., waxes, gum arabic, etc. or mixtures thereof which are per se powders or are powdered. Preferred are inorganic coloring matters such as talc, magnesium carbonate, magnesium silicate, magnesium oxide, aluminum hydroxide, etc., hydroxypropyl cellulose or starches. Any other materials which can be deposited in the impressed valley portion may also be used.

The tablets impressed with marks, etc. (which will be called merely "impressed tablets" hereinafter) have no special limitation in their shape, size, etc. and may be either uncoated tablets or coated tablets as long as they have marks impressed thereon. However, adherence of the deposition material to the impressed valley portion of the latter tablets, i.e., those having a coating thereon is better than that of uncoated tablets. Therefore, in order to obtain clearer impressed marks, it is preferred to use the tablets which are applied with a coating in such a manner that the impressed valley portion is not filled up with the coating.

The tablets of this invention may be obtained by depositing the deposition material in the impressed valley portion. For this purpose, firstly the impressed tablets and the deposition material are mixed and contacted with each other at substantially dry state in a suitable vessel. One method for the mixing and contacting the tablets with the deposition material comprises introducing the impressed tablets and the deposition material in the generally used coating pan or throughflow drying type pan and operating the pan until the deposition material has been uniformly deposited in the impressed valley portion.

Amount of the deposition material to the tablets at mixing and contacting varies depending on properties of the surface of the tablets and kind of the deposition material and usually may be 5% or less. Of course, addition of more than 5% causes no problems.

In this way, the deposition material is uniformly deposited in the impressed valley portion of the marks.

Then, preferably, the excess deposition material other than deposited in the impressed valley portion is removed. This removal of the excess deposition material may be carried out, for example, by sifting the excess deposition material from the tablets with an ordinary sieve, by rubbing the surface of the tablets with a brush and by passing air therethrough, for example, by inserting into layer of tablets an exhaust tube of a coating pan the open tip of which is covered with a gauze or a net and removing the excess deposition material with suction air. More preferably, the excess deposition material may be easily removed by simultaneous charging and discharging of air using a through-flow type pan or apparatus.

That is, as is clear from the above explanation or examples given hereinafter, the method for making the tablets according to this invention comprises mixing and contacting the impressed tablets with the deposition material at substantially dry state to uniformly deposit the deposition material in the impressed valley portion of the tablets and then removing excess deposition material other than deposited in the impressed valley portion. Thus obtained tablets having impressed valley portion in which a deposition material is deposited have, as they are, sufficiently clear impressed marks, but if necessary, they may be further applied with a desired coating such as water-soluble, gastric juice soluble or enteric coating. Amount of the coating has no special limitation as long as it does not cause loss of the difference in color tone which brings about the clear impressed marks of this invention. Any materials which are generally used for coating of tablets may be used as components of the coating. As examples of coating agents, mention may be made of sucrose, methyl cellulose, hydroxypropylmethyl cellulose, hydroxypropyl cellulose, polyvinyl acetal diethylaminoacetate, carboxymethylethyl cellulose, cellulose acetate phthalate, hydroxypropylmethyl cellulose phthalate, methacrylic acid and ethyl acrylate copolymers, etc. As examples of plasticizers, mention may be made of polyethylene glycol, propylene glycol, glycerine, triacetin, castor oil, myvacet, shellac, etc. and as examples of coloring agents, mention may be made of food dyestuff, food lake dyestuff, titanium oxide, talc, kaolin, etc. Any coating solvents which are generally used such as water, ethanol, acetone, methylene chloride, isopropyl alcohol, etc. may be used. As coating method, there may be used any methods such as pouring of coating solution, spraying by air spray or airless spray gun, etc. Any of coating devices recently used for coating such as through-flow type coating pans or fluidization type coating devices may be used besides the conventionally used so-called coating pans. The coating conditions are utterly the same as those conventionally employed.

When a mixture of a wax and a powdery material or powder is used as the deposition material in this invention, adherence of the deposition material and the impressed tablets in the impressed valley portion can be further increased by heating the wax mixture after deposition in the valley portion to 40°–90° C. to thereby melt the wax. Preferred example of this method comprises depositing the wax mixture in the impressed portion and then removing an excess deposition material other than deposited in the valley portion by the above mentioned method before heating it to 40°–90° C. Thus obtained impressed tablets may be coated, if necessary. The heating to 40°–90° C. may be carried out by the ordinary drying method for tablets such as by passing warm air therethrough, by leaving them in a warming chamber, etc. The waxes used for this purpose are those which are solid at room temperature and have a melting point of 90° C. or less. Examples of the waxes are oils and fats such as hydrogenated oil (Lubri Wax ®), etc., bees wax, Carnauba wax, etc., hydrocarbons such as paraffins, higher alcohols such as cetyl alcohol, stearyl alcohol, etc., higher fatty acids such as stearic acid, palmitic acid, etc., polyhydric alcohols such as polyethyleneglycol, etc., fatty acid esters of polyhydric alcohols, e.g., sucrose fatty acid esters such as sucrose monopalmitate, sucrose monostearate, sucrose tripalmitate, sucrose tristearate, etc., sorbitan fatty acid esters such as sorbitan monostearate, sorbitan monopalmitate, sorbitan tristearate, etc.

The waxes may be used in an amount of 70% or less, preferably 5–50% of other powdery material or powder.

Preferred examples of said powdery material or powder are inorganic colorants, starches, celluloses or mixtures thereof with colorants. These may be deposited in the same manner as mentioned hereinbefore.

Thus obtained tablets have clearer marks for identification than the conventional tablets and may be subjected to polishing, etc. to give gloss.

This invention will be illustrated by the following examples wherein part is by weight.

EXAMPLE 1

(Preparation of tablets having marks impressed thereon)

| Lactose | 70 parts |
| Corn starch | 25 parts |
| Carboxymethyl cellulose calcium | 5 parts |

The above components were mixed and to the mixture was added 20 parts of 5% corn starch paste. These were kneaded and then dried to obtain granules, to which 0.5 part of magnesium stearate was added followed by mixing. From the mixture were prepared tablets having a diameter of 8 mm and a weight (per one tablet) of 190 mg and impressed with a figure "50" (width: 0.3 mm, depth: 0.15 mm and angle: 60°) on the surface by a rotary tablet machine.

(Preparation of coating solution)

| Polyvinyl acetal diethylaminoacetate | 6 parts |
| Polyethylene glycol 6000 | 1 part |
| Titanium oxide | 0.2 part |
| Methanol | 93 parts |

The above components were stirred until they were homogeneously dispersed or dissolved to prepare a coating solution.

(Procedure)

1.5 kg of the tablets and 70 g of a deposition material which was a mixture of 100 parts of talc and one part of FD & C yellow No. 5 aluminum lake dyestuff were charged in a coating pan of about 30 cm in diameter and the coating pan was operated for 10 minutes to uniformly deposit said deposition material in the valley portion of the impressed figure. Then, the tablets were taken out from the coating pan and excess deposition material was removed by sifting by a No. 12 sieve. Then, the tablets were again charged in the coating pan to carry out coating with said coating solution according to a conventional method to obtain tablets having a coating amount of about 4.1 mg per one tablet and having the impressed figure colored in reddish yellow when 600 g of said coating solution had been sprayed.

EXAMPLE 2

(Preparation of coating solution)

| Hydroxypropylmethyl cellulose | 7 parts |
| Titanium oxide | 1 part |
| Water | 92 parts |

The above components were stirred until they were homogeneously dispersed or dissolved to obtain a coating solution.

(Procedure)

10 kg of the same tablets as used in Example 1 were charged in High-Coater ® (through-flow drying type coating device, HCT-60, manufactured by Freund Sangyo K.K.) and coating was effected according to the conventional method to obtain tablets having a coating amount of about 5.1 mg per one tablet when 5 kg of said coating solution was sprayed. Then, after discontinuation of charging and discharging of air, to the tablets was added 200 g of a deposition material prepared by mixing 100 parts of kaolin, 3 parts of FD & C blue No. 2 aluminum lake dyestuff and 10 parts of corn starch and the pan was operated for 5 minutes to uniformly deposit the deposition material in the impressed valley figure portion. Then, excess deposition material was removed by operating the pan for 10 minutes with passing air therethrough by charging and discharging of air to obtain tablets having the impressed figure colored in blue.

EXAMPLE 3

(Preparation of coating solution)

| Hydroxypropylmethyl cellulose phthalate | 5 parts |
| Titanium oxide | 0.3 part |
| Methylene chloride | 45 parts |
| Ethanol | 45 parts |

The above components were stirred until they were homogeneously dispersed or dissolved to obtain a coating solution (Procedure)

10 kg of the same tablets as used in Example 1 were charged in High-Coater ® (HCT-60) to coat them with the same coating solution as used in Example 2 according to a conventional method to obtain tablets having a coating amount of about 2.2 mg per one tablet when 2 kg of the coating solution was sprayed. Then, after discontinuation of charging and discharging of air, to the tablets was added 200 g of a deposition material prepared by mixing 100 parts of kaolin, 3 parts of FD & C yellow No. 5 aluminum lake dyestuff and 20 parts of lactose and the pan was operated for 5 minutes to uniformly deposit the deposition material in the impressed valley figure portion. Thereafter, the pan was further operated for 10 minutes with passing air therethrough by charging and discharging of air to remove excess deposition material. Then, the tablets were coated with 32 kg of said coating solution prepared in this Example according to a conventional method to obtain tablets having a coating amount of about 23.0 mg per one tablet and having the impressed figure colored in reddish yellow. These tablets met the test specification for enteric coated preparations disclosed in the Japanese Pharmacopoeia.

EXAMPLE 4

(Preparation of coating solution)

| Coating solution - 1 | |
| --- | --- |
| Hydroxypropylmethyl cellulose | 6 parts |
| Titanium oxide | 0.3 part |
| Red No. 103 dyestuff (The Japanese Standard of Food Additives) | 1.5 parts |
| Polyethylene glycol 400 | 1.5 parts |
| Water | 90 parts |
| Coating solution - 2 | |
| Hydroxypropylmethyl cellulose | 7 parts |
| Water | 93 parts |

The above components were stirred until they were homogeneously dispersed or dissolved to obtain the coating solution - 1 and the coating solution - 2.

(Procedure)

15 kg of the same tablets as used in Example 1 were charged in High-Coater ® (HCT-60) to coat them with coating solution - 1 by the conventional method to obtain tablets having a coating amount of about 2.1 mg per one tablet when 3 kg of the coating solution - 1 was sprayed. Then, after discontinuation of charging and discharging of air, 300 g of talc was added to the tablets and the pan was operated for 5 minutes to uniformly deposit the talc in the impressed valley figure portion. Thereafter, the pan was further operated for 2 minutes with passing air therethrough by charging and discharging of air to remove excess talc. Then, coating of the tablets was carried out using 1 kg of said coating solution - 2 to obtain reddish brown tablets having a coating amount of about 2.7 mg per one tablet and having the impressed figure colored in white.

The above procedure was repeated except that talc was replaced with 300 g of magnesium silicate, magnesium oxide or aluminum hydroxide to obtain reddish brown tablets having white impressed figure in each case.

EXAMPLE 5

(Preparation of coating solution)

| Hydroxypropyl cellulose | 8 parts |
| FD & C yellow No. 5 aluminum lake dyestuff | 1 part |
| Glycerine | 0.5 part |
| Water | 90 parts |

The above components were stirred until they were homogeneously dispersed or dissolved to obtain a coating solution.

(Procedure)

10 kg of the same tablets as used in Example 1 were charged in High-Coater ® (HCT-60) to coat them with said coating solution by a conventional method to obtain tablets having a coating amount of about 4.2 mg per one tablet when 4 kg of the coating solution was sprayed. Then, after discontinuation of charging and discharging of air, to the tablets was added 300 g of a deposition material obtained by mixing 100 parts of talc and 4 parts of FD & C blue No. 1 aluminum lake dyestuff and the pan was operated for 5 minutes to uniformly deposit the material in the impressed valley figure portion. Then, the pan was further operated for 10 minutes with passing air by charging and discharging of air to obtain reddish yellow tablets having blue impressed figure portion.

EXAMPLE 6

(Preparation of tablets having impressed mark)

| Lactose | 70 parts |
| Corn starch | 30 parts |
| FD & C blue No. 1 aluminum lake dyestuff | 0.5 part |

The above components were mixed and to the mixture was added 20 parts of 5% corn starch paste. They were kneaded and then dried to obtain granules. 0.5 part of magnesium stearate was added thereto and mixed. From the mixture, blue tablets having a diameter of 8 mm and a weight (per one tablet) of 200 mg and having an impressed figure "246" (width: 0.32 mm, depth: 0.16 mm and angle: 60°) on their surface were produced by a rotary tablet machine.

(Preparation of coating solution)

| Methyl cellulose | 4 parts |
|---|---|
| Water | 96 parts |

The above components were stirred until they were dissolved to obtain a coating solution.

(Procedure)

4 kg of said tablets and 170 g of heavy magnesium carbonate were charged in a coating pan of about 40 cm in diameter and the coating pan was operated for 10 minutes to uniformly deposit the heavy magnesium carbonate in the impressed valley figure portion. Then, an exhaust tube the opening end of which was covered with a gauze was inserted in the tablets to remove excess heavy magnesium carbonate by suction air. Thereafter, the tablets were coated by spraying 600 g of said coating solution thereon by a conventional method to obtain blue tablets having white impressed figure portion.

EXAMPLE 7

(Preparation of coating solution)

| Hydroxypropylmethyl cellulose | 6 parts |
|---|---|
| Titanium oxide | 0.2 part |
| Yellow iron oxide | 1.5 parts |
| Polyethylene glycol 6000 | 3 parts |
| Water | 90 parts |

The above components were stirred until they were homogeneously dispersed or dissolved to obtain a coating solution.

(Procedure)

From the granules prepared in Example 1, tablets having a diameter of 8.5 mm and a weight (per one tablet) of 210 mg and having an impressed bisect line (width: 0.5 mm, depth: 0.25 mm and angle: 90°) on their surface were produced by a rotary tablet machine. 10 kg of these tablets were charged in High-Coater ® (HCT-60) to coat them with said coating solution by a conventional method to obtain tablets having a coating amount of about 5 mg when 3 kg of the coating solution was sprayed. Then, after discontinuation of charging and discharging of air, 400 g of calcium carbonate was added to the tablets and the pan was operated for 10 minutes to uniformly deposit calcium carbonate in the impressed valley line portion. Then, the pan was further operated for 2 minutes with passing air therethrough by charging and discharging of air to remove excess calcium carbonate. Then, these tablets were coated with 1 kg of the coating solution used in Example 6 by a conventional method to obtain yellowish brown tablets having a coating amount of about 6 mg per one tablet and having a white impressed line portion.

EXAMPLE 8

(Preparation of coating solution)

| Coating solution - 1 | |
|---|---|
| Hydroxypropylmethyl cellulose | 7 parts |
| Iron sesquioxide | 2 parts |
| Water | 91 parts |
| Coating solution - 2 | |
| Eudragit L30D55 ® (aqueous dispersion of methacrylic acid and ethyl acrylate copolymer manufactured by Rohm Pharma GMBH) | 50 parts |
| Water | 50 parts |

The above components were stirred until they were homogeneously dispersed and dissolved to obtain coating solutions - 1 and - 2.

(Procedure)

From the granules prepared in Example 6, tablets having a diameter of 9 mm and a weight (per one tablet) of 280 mg and having an impressed figure "510" (width: 0.2 mm, depth: 0.1 mm and angle: 50°) on their surface were prepared by a rotary tablet machine. 12 kg of these tablets were charged in High-Coater ® (HCT-60) to coat them with said coating solution - 1 by a conventional method to obtain tablets having a coating amount of about 4 mg per one tablet when 3 kg of the coating solution was sprayed. Then, after discontinuation of charging and discharging of air, 600 g of lactose was added to the tablets and the pan was operated for 2 minutes to uniformly deposit the lactose in the impressed valley figure portion. Thereafter, the excess lactose was removed with passing air therethrough by charging and discharging of air. Then, these tablets were coated with 7 kg of said coating solution - 2 by a conventional method to obtain reddish brown tablets having a coating amount of about 2.1 mg per one tablet and having a white figure portion.

The above procedure was repeated using 600 g of hydroxypropyl cellulose (L-HPC ® manufactured by Shinetsu Chemical Co., Ltd.) in place of the lactose to obtain reddish brown tablets having a white figure portion.

These tablets met the test specification for enteric coated preparations mentioned in Japanese Pharmacopoeia.

EXAMPLE 9

(Preparation of coating solution)

| Hydroxypropyl cellulose | 5 parts |
|---|---|
| Stearic acid | 0.5 part |
| Ethyl alcohol | 40 parts |
| Methylene chloride | 60 parts |

The above components were stirred until they were homogeneously dissolved to obtain a coating solution.

(Procedure)

From the granules prepared in Example 1, tablets having a diameter of 10 mm and a weight (per one tablet) of 360 mg and having an impressed figure "135" (width: 0.43 mm, depth: 0.23 mm and angle: 60°) on their surface were prepared by a rotary tablet machine. 15 kg of these tablets were charged in High-Coater ®

(HCT-60) to coat them with said coating solution by a conventional method to obtain tablets having a coating amount of about 2 mg per one tablet when 2.5 kg of the coating solution was sprayed. After discontinuation of charging and discharging of air, to these tablets was added 500 g of a deposition material prepared by adding about 10 parts of water to 100 parts of mannitol and 5 parts of FD & C yellow No. 5 dyestuff, mixing and drying them and grounding them and the pan was operated for 2 minutes to uniformly deposite the material in the impressed valley figure portion. Then, the pan was further operated for one minute with passing air therethrough by charging and discharging of air to remove excess material. Thereafter, these tablets were further coated with 1 kg of said coating solution by a conventional method to obtain tablets having a coating amount of about 3 mg per one tablet and having reddish yellow impressed figure portion.

EXAMPLE 10

(Preparation of coating solution)

| Hydroxypropylmethyl cellulose | 5 parts |
| --- | --- |
| Iron sesquioxide | 1 part |
| Talc | 0.5 part |
| Water | 90 parts |

The above components were stirred until they were homogeneously dispersed or dissolved to obtain a coating solution.

(Procedure)

From the granules prepared in Example 1, tablets having a diameter of 8 mm and a weight (per one tablet) of 200 mg and impressed with a figure "124" (width: 0.36 mm, depth: 0.18 mm and angle: 60°) on the surface were prepared by a rotary tablet machine. 12 kg of these tablets were charged in High-Coater ® (HCT-60) to coat them with said coating solution by a conventional method to obtain tablets having a coating amount of about 1 mg per one tablet when 1.5 kg of said coating solution was sprayed. After discontinuation of charging and discharging of air, to the tablets was added 200 g of a mixture of 10 parts of talc and 1 part of a sucrose fatty acid ester manufactured (DKF-50 ® manufactured by Daiichi Kogyo Seiyaku Co., Ltd.) and the pan was operated for 3 minutes to uniformly deposit the mixture in the impressed valley figure portion. Thereafter, the pan was further operated for 1 minute with passing air therethrough by charging and discharging of air to remove excess mixture followed by passing therethrough hot air of 90° C. for 15 minutes to obtain reddish brown tablets having a white impressed figure portion.

The above procedure was repeated using a hydrogenated oil (Lubri Wax 101 ® manufactured by Freund Sangyo K.K.) in place of the sucrose fatty acid ester to obtain reddish brown tablets having a white impressed figure portion.

EXAMPLE 11

(Preparation of coating solution)

| Hydroxypropylmethyl cellulose | 6 parts |
| --- | --- |
| Yellow iron oxide | 1.5 parts |
| Glycerin | 0.5 part |
| Water | 90 parts |

The above components were stirred until a homogeneous dispersion or solution was obtained to prepare a coating solution.

(Procedure)

15 kg of the same tablets as used in Example 1 were charged in High-Coater ® (HCT-60) to coat them with said coating solution by a conventional method to obtain tablets having a coating amount of about 2 mg per one tablet when 2.5 kg of the coating solution was sprayed. After discontinuation of charging and discharging of air, to the tablets was added 600 g of a ground mixture of 5 parts of magnesium carbonate and 1 part of polyethylene glycol 6000 and the pan was operated for 2 minutes to uniformly deposit said mixture in the impressed valley figure portion. Thereafter, the pan was further operated for 1 minute with passing air therethrough by charging and discharging of air to remove excess mixture followed by passing hot air of 80° C. for 15 minutes to obtain yellowish brown tablets having a white impressed figure portion.

EXAMPLE 12

(Preparation of coating solution)

| Hydroxypropyl cellulose | 7 parts |
| --- | --- |
| FD & C yellow No. 5 aluminum lake dyestuff | 0.5 part |
| Glycerin | 0.5 part |
| Water | 90 parts |

The above components were stirred until they were homogeneously dispersed or dissolved to prepare a coating solution.

(Procedure)

From the granules prepared in Example 1, tablets having a diameter of 9 mm and a weight (per one tablet) of 280 mg and impressed with a figure "510" (width: 0.2 mm, depth: 0.1 mm and angle: 50°) on the surface were prepared by a rotary tablet machine. 4 Kg of these tablets were charged in a coating pan of about 40 cm in diameter and were coated with 1.2 kg of said coating solution by a conventional method. Then, 180 g of mixture of 1 part of stearic acid and 1 part of magnesium oxide was added to the tablets and the pan was operated for 5 minutes to uniformly deposit the mixture in the impressed valley figure portion. Thereafter, an exhaust tube the opening end of which was covered with a gauze was inserted in the tablets to remove excess mixture by suction air. The resulting tablets were charged in a chamber dryer and heated at 80° C. for 5 hours to obtain reddish yellow tablets having a white impressed figure portion.

We claim:

1. A tablet having a clear mark impressed thereon wherein the impressed valley portion has a powdery material uniformly deposited therein which is different in color tone from the portion other than the mark portion, said tablet having a sub-coating which has previously been applied in such manner that the impressed valley portion is not filled up with the coating, the deposition material having been deposited in a substantially dry state.

2. A tablet according to claim 1 wherein the valley portion is completely free of the different color on other portions of the tablet and the other portions are completely free of the color on the valley portion.

3. A tablet according to claim 1 which has been prepared by a process wherein excess deposition material other than that deposited in the impressed valley portion is removed.

4. A tablet according to claim 3 wherein the powdery material is a starch, a sugar, an inorganic coloring matter, a cellulose, a dye, a wax, mannitol, or gum arabic and is present in an amount of 5% or less, the tablet having been subsequently coated with a contrasting color from the valley color after deposition of the material, the constrasting color being applied in a coating of hydroxypropylmethyl cellulose or hydroxypropyl cellulose.

5. A tablet according to claim 4 wherein the powdery material is selected from the group consisting of corn starch, wheat starch, potato starch, lactose, sucrose, mannitol, calcium sulfate, calcium phosphate, calcium carbonate, magnesium carbonate, magnesium silicate, magnesium oxide, aluminum hydroxide, titanium oxide, talc, kaolin, bentonite, methyl cellulose, ethyl cellulose, carboxymethylethyl cellulose, hydroxypropylmethyl cellulose, hydroxypropylethyl cellulose phthalate, hydroxypropyl cellulose, crystalline cellulose, a food dye, a food-like dyestuff, and a wax.

6. A tablet according to claim 1 wherein the tablets before deposition of the material has a coating thereon.

7. A tablet according to claim 1 wherein the powdery material is inorganic colorant, hydroxypropyl cellulose or starch.

8. A tablet according to claim 7 wherein the inorganic colorant is talc, magnesium carbonate, magnesium silicate, magnesium oxide or aluminum hydroxide.

9. A tablet according to claim 1 wherein the powdery material is a mixture of a wax which is solid at room temperature and has a melting point of 90° C. or less with other powdery material or powder.

10. A tablet according to claim 9 wherein amount of the wax is 5 to 50% of other powdery material.

* * * * *